United States Patent [19]

Munakata et al.

[11] 4,244,952
[45] Jan. 13, 1981

[54] IMIDAZO[2',1':2,3]-THIAZOLO[5,4-C]PYRIDINES AND COMPOSITION THEREOF FOR TREATING IMMUNE DISEASES

[75] Inventors: Tomohiko Munakata; Kazumi Saeki; Kazuhiro Goto, all of Nakatsu; Kiyoteru Ikegami, Yoshio, all of Japan

[73] Assignee: Yoshitomi Pharmaceutical Industries, Ltd., Osaka, Japan

[21] Appl. No.: 79,723

[22] Filed: Sep. 28, 1979

[30] Foreign Application Priority Data

Sep. 28, 1978 [JP] Japan ................................ 53-120041
Oct. 4, 1978 [JP] Japan ................................ 53-123034

[51] Int. Cl.³ ...................... A61K 31/44; C07D 513/14
[52] U.S. Cl. ........................................ 424/256; 546/83; 546/114
[58] Field of Search ........................... 546/83; 424/256

[56] References Cited

U.S. PATENT DOCUMENTS

| 3,274,209 | 9/1966 | Raeymaekers et al. | 548/154 |
| 3,463,786 | 8/1969 | Bullock | 548/154 |
| 4,122,083 | 10/1978 | Sundeen et al. | 546/64 |

OTHER PUBLICATIONS

*Chemical Abstracts*, 87: 68236h (1977) [Khadse, B., et al., Bull. Haffkine Inst. 1977, 5(1), 9–16].

*Primary Examiner*—Henry R. Jiles
*Assistant Examiner*—Richard A. Schwartz
*Attorney, Agent, or Firm*—Sughrue, Rothwell, Mion, Zinn and Macpeak

[57] ABSTRACT

A heterocyclic compound of the formula:

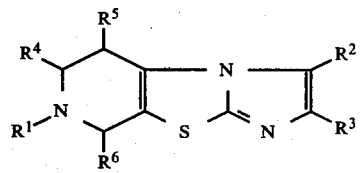

or a pharmaceutically acceptable acid addition salt thereof, wherein $R^1$ is hydrogen, $C_{1-4}$ alkyl, $C_{1-4}$ alkoxycarbonyl, formyl, nitroso, acyl, phenacyl, aralkyl, α-(benzyloxycarbonyl)benzyl or α-carboxybenzyl; each of $R^2$ and $R^3$ is hydrogen, $C_{1-4}$ alkyl or aryl; and all of $R^4$, $R^5$ and $R^6$ are hydrogens, or both $R^1$ and $R^6$, and $R^4$ and $R^5$ together form single bonds; in which definitions the term "acyl", "phenacyl", "aralkyl" or "aryl" means that it may be substituted by at least one substituent at any position(s) on the aromatic nucleus, each substituent being independently selected from $C_{1-4}$ alkyl, $C_{1-4}$ alkoxy, halogen, hydroxyl, phenyl, nitro, trifluoromethyl, methylthio, methanesulfonyl and methylenedioxy. Such compounds are useful as drugs for treating immune diseases.

13 Claims, No Drawings

IMIDAZO[2',1':2,3]-THIAZOLO[5,4-C]PYRIDINES AND COMPOSITION THEREOF FOR TREATING IMMUNE DISEASES

The present invention relates to novel and therapeutically valuable heterocyclic compounds or pharmaceutically acceptable acid addition salts thereof and pharmaceutical compositions containing the same.

The heterocyclic compounds of the present invention are represented by the following formula:

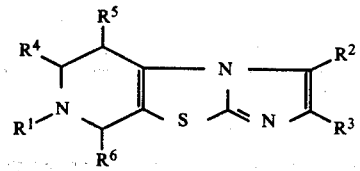

(I)

wherein:
- $R^1$ is hydrogen, $C_{1-4}$ alkyl (e.g. methyl, ethyl, propyl, isopropyl or butyl), $C_{1-4}$ alkoxycarbonyl (e.g. methoxy-, ethoxy-, propoxy- or butoxycarbonyl), formyl, nitroso, acyl (e.g. acetyl, propionyl, butyryl, benzoyl or phenylacetyl), phenacyl, aralkyl (e.g. benzyl or phenethyl), α-(benzyloxycarbonyl)benzyl or α-carboxybenzyl;
- each of $R^2$ and $R^3$ is hydrogen, $C_{1-4}$ alkyl (e.g. methyl, ethyl, propyl, isopropyl or butyl) or aryl (e.g. phenyl); and
- all of $R^4$, $R^5$ and $R^6$ are hydrogens, or both $R^1$ and $R^6$, and $R^4$ and $R^5$ together form single bonds;
- in which definitions the term "acyl", "phenacyl", "aralkyl" or "aryl" means that it may be substituted by at least one substituent at any position(s) on the aromatic nucleus, each substituent being independently selected from $C_{1-4}$ alkyl (e.g. methyl, ethyl, propyl, isopropyl or butyl), $C_{1-4}$ alkoxy (e.g. methoxy, ethoxy, propoxy or butoxy), halogen (e.g. fluorine, chlorine or bromine), hydroxyl, phenyl, nitro, trifluoromethyl, methylthio, methanesulfonyl and methylenedioxy.

For easy understanding, formula (I) mentioned above can be represented as follows:

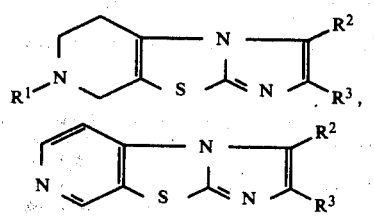

wherein each symbol is as defined above.

Preferable compounds of the formula (I) are those wherein $R^2$ is hydrogen and $R^3$ is hydrogen or phenyl which may be substituted by at least one substituent at any position(s) on the aromatic nucleus, each substituent being independently selected from $C_{1-4}$ alkyl, $C_{1-4}$ alkoxy, halogen, hydroxyl, phenyl, nitro, trifluoromethyl, methylthio, methanesulfonyl and methylenedioxy.

More preferable compounds of the formula (I) are those wherein $R^2$ is hydrogen and $R^3$ is hydrogen or phenyl which is unsubstituted or substituted by halogen, nitro or methylthio.

The compounds of formula (I) can be prepared by one of the following Methods (i) to (iv):

Method (i): In the case of compounds (I-a), the reaction of a compound of the formula:

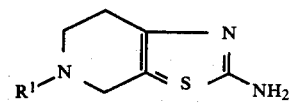

wherein $R^1$ is as defined above, with a compound of the formula:

$$R^3COCHR^2$$

wherein $R^2$ and $R^3$ are as defined above and X is halogen. Method (ii): In the case of compounds (I-a) wherein $R^1$ is hydrogen, the reaction of a compound of the formula:

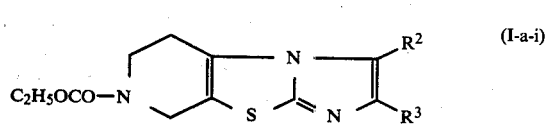

(I-a-i)

wherein $R^2$ and $R^3$ are as defined above, with potassium hydroxide in ethanol or with a solution of hydrobromic acid in acetic acid.

Method (iii): In the case of compounds (I-a) wherein $R^1$ is other than hydrogen, the reaction of a compound of formula (I-a) wherein $R^1$ is hydrogen with an alkylating agent, an aralkylating agent, an acylating agent, a phenacylating agent, a formylating agent or nitrosating agent.

The reactions of Methods (i) to (iii) are usually carried out in an inert solvent at a temperarure of room temperature to about 200° C. The solvent includes an alcohol (e.g. methanol, ethanol, propanol, isopropanol, butanol, isobutanol, sedondary butanol, tertiary butanol or methyl cellosolve), an ether (e.g. diethyl ether, isopropyl ether, dibutyl ether, dioxane, tetrahydrofuran, monoglyme or diglyme), an ester (e.g. ethyl acetate or butyl acetate), an amide (e.g. dimethylformamide or dimethylacetamide), a hydrocarbon (e.g. benzene, toluene, xylene, petroleum benzin or ligroin), a halo-hydrocarbon (e.g. methylene chloride, chloroform, carbon tetrachloride, dichloroethane, tetrachloroethane or chlorobenzene), an amine (e.g. pyridine, picoline, dimethylaniline or triethylamine), an organic acid (e.g. formic acid, acetic acid or propionic acid), dimethylsulfoxide and a mixture thereof. The reaction can also be carried out without solvent. Method (iv): In the case of compounds (I-b), the dehydrogenation reaction of a compound of formula (I-a) wherein $R^1$ is hydrogen.

The reaction is usually carried out in a solvent such as toluene, xylene, mesitylene, naphthalene or decalin in the presence of a catalyst for dehydrogenation such as sulfur, selenium, palladium carbon, palladium asbestos, platinum, platinum carbon or nickel under heating at 100°–350° C. The reaction can also be carried out without solvent.

The compounds of formula (I) can be converted into the acid addition salts by treating a compound of formula (I) previously dissolved in a solvent such as methanol or ethanol with an inorganic acid such as hydrochloric, hydrobromic, phosphoric or sulfuric acid or with an organic acid such as tartaric, citric, maleic, fumaric, malic, β-naphthalenesulfonic or pamoic acid.

The compounds of formula (I) and pharmaceutically acceptable acid addition salts thereof have immunomodulatory activities as shown, for example, by the following tests:

TEST METHODS

(I) Activity for potentiating immune response in dd-mice

As test animals, male dd-strain mice (8 week old) were used by dividing them into groups of 6 members. Each mouse was orally administered once a day with cyclophosphamide (CY) at a dose of 20 mg/kg 1 and 0 day before the sensitization. The sensitization (day 0) was made by the intravenous injection of the antigen; $1 \times 10^8$ sheep red blood cells (SRBC). Each mouse was orally administered with test compounds (day 0-4). Five days after the sensitization, the number of rosette forming cells (RFC) in the spleen and thymus was measured in a usual manner.

The number of RFC per spleen and thymus of the mouse in the group treated with CY alone was reduced significantly. The reduction of RFC both in the spleen and thymus was restored by the treatment with test compounds as shown in Table I.

(II) Activity for suppressing immune response in BALB/c mice

As test animals, female BALB/c-strain mice (6 week old) were used by dividing them into groups of 6 members.

The sensitization (day 0) was made by the intraperitoneal injection the antigen; $5 \times 10^8$ sheep red blood cells (SRBC). Each mouse was orally administered with test compounds at day 0 and 1. Four days after the sensitization, the number of rosette forming cells (RFC) in the spleen and thymus was measured in a usual manner.

The treatment with the test compound resulted in the reduction of RFC in the spleen and thymus as shown in Table II.

(III) Acute toxicity

Acute toxicity of the test compound was determined using male dd-strain mice (8 week old) as test animals. The test compound was administered orally or intraperitoneally. The results are shown in Table III.

TEST COMPOUNDS

Compound A: 7-ethoxycarbonyl-2-(4-nitrophenyl)-5,6,7,8-tetrahydroimidazo[2',1':2,3]thiazolo[5,4-c]pyridine Compound B: 7-(4-nitrobenzyl)-5,6,7,8-tetrahydroimidazo[2',1':2,3]thiazolo-[5,4-c]pyridine

RESULTS

Table I

| Treatment | Dose (mg/kg) | RFC/organ ($\times 10^4$) Spleen | Thymus |
|---|---|---|---|
| Control | 0 | 337** | 3.92** |
| CY (20 mg/kg) | 20 | 101 | 0.44 |
| +Compound A | 1 | 169 | 3.33* |
| +Compound A | 10 | 220 | 3.11* |
| CY (20 mg/kg) | | | |
| +Compound B | 1 | 291** | 2.00 |
| +Compound B | 10 | 135 | 1.56 |

*P < 0.05,
**P < 0.01 significant vs. CY treatment

Table II

| Treatment | Dose (mg/kg) | RFC/organ ($\times 10^4$) Spleen | Thymus |
|---|---|---|---|
| Control | 0 | 173 | 0.96 |
| Compound A | 30 | 174 | 0.00** |
| Compound B | 30 | 104 | 0.14** |

**P < 0.01 significant vs. control

Table III

| Test compound | Route | $LD_{50}$ (mg/kg) |
|---|---|---|
| A | p.o. | 1,000 |
| | i.p. | 600 |
| B | p.o. | 600 |
| | i.p. | 600-1,000 |

In view of the tests above, the compounds of formula (I) and pharmaceutically acceptable acid addition salts thereof are potent in immunomodulatory activities, so that it can be said that the compounds of the present invention are useful as drugs for treating immune diseases such as rheumatoid arthritis, allergy, autoimmune diseases or bacterial infectious diseases.

The compounds of formula (I) and pharmaceutically acceptable acid addition salts thereof can be administered safely as immunomodulators, either alone or in the form of a pharmaceutical preparation with a suitable and conventional carrier or adjuvant, administered orally, without harmful side effects to the patients.

The pharmaceutical composition can take the form of tablets, granules, powder or capsules, for oral administration, of injectable solution for subcutaneous or intramuscular administration. The choice of carrier is determined by the preferred form of administration, the solubility of the compounds and standard pharmaceutical practice.

FORMULATION EXAMPLE 50 mg tablets are prepared from the following compositions:

| | |
|---|---|
| Compound A | 50.0 mg |
| Lactose | 98.0 mg |
| Microcrystalline cellulose | 15.0 mg |
| Corn starch | 20.0 mg |
| Calcium carboxymethyl cellulose | 20.0 mg |
| Methyl cellulose | 1.5 mg |
| Talc | 4.5 mg |
| Magnesium stearate | 1.0 mg |
| | 210.0 mg |

The daily dose of the compounds of formula (I) or pharmaceutically acceptable acid addition salts thereof for human adults usually ranges from 50–500 mg, but it may vary depending upon the age, body weight, and/or severity of the condition to be treated as well as the response to the medication.

The present invention will be better understood from the following examples, but they are not to be construed as limiting the present invention.

EXAMPLE 1

A mixture of 4.5 g of 2-amino-6-ethoxycarbonyl-4,5,6,7-tetrahydrothiazolo[5,4-c]pyridine, 4 g of phenacyl bromide and 50 ml of n-butanol was heated at 70°–75° C. for 3 hours. After the solvent was distilled off, the precipitated crystals were filtered off and washed with a mixture of ethanol and n-hexane to give 5 g of 7-ethoxycarbonyl-2-phenyl-5,6,7,8-tetrahydroimidazo[2',1':2,3]thiazolo[5,4-c]pyridine hydrobromide, melting at 225°–226° C. with decomposition. The hydrobromide was treated with an aqueous ammonium to give the free base, melting at 111°–112° C.

EXAMPLE 2

A mixture of 4.1 g of 7-ethoxycarbonyl-2-phenyl-5,6,7,8-tetrahydroimidazo[2',1':2,3]thiazolo[5,4-c]pyridine hydrobromide and 50 ml of a solution of hydrobromic acid in acetic acid (20% (w/w) hydrobromic acid) was heated on a boiled water bath for 2 hours. The precipitated crystals were filtered off and washed with a mixture of ethanol and n-hexane to give 3.9 g of 2-phenyl-5,6,7,8-tetrahydroimidazo[2',1':2,3]thiazolo[5,4-c]pyridine dihydrobromide, melting at 315°–316° C. with decomposition.

EXAMPLE 3

A mixture of 11.4 g of 2-amino-6-ethoxycarbonyl-4,5,6,7-tetrahydrothiazolo[5,4-c]pyridine, 13.8 g of p-phenylbromoacetophenone and 80 ml of n-butanol was heated at 105° C. for 2 hours. After cooling, the precipitated crystals were filtered off and recrystallized from a mixture of ethanol and dimethylsulfoxide to give 8.1 g of 7-ethoxycarbonyl-2-(4-biphenylyl)-5,6,7,8-tetrahydroimidazo[2',1':2,3]thiazolo[5,4-c]pyridine hydrobromide, melting at 172°–174° C.

EXAMPLE 4

The product of Example 3 was treated according to the procedure of Example 2 to give 2-(4-biphenylyl)-5,6,7,8-tetrahydroimidazo[2',1':2,3]thiazolo[5,4-c]pyridine dihydrobromide, melting at 302°–304° C. with decomposition.

EXAMPLE 5

A mixture of 22.7 g of 2-amino-6-ethoxycarbonyl-4,5,6,7-tetrahydrothiazolo[5,4-c]pyridine, 23.3 g of p-chlorophenacyl bromide and 250 ml of n-butanol was heated at 70°–75° C. for 5.5 hours. After cooling, the precipitated crystals were filtered off and suspended in chloroform. Triethylamine was added to the suspension till the crystals were completely dissolved. The chloroform solution was washed with water and concentrated. The residue was recrystallized from ethanol to give 15 g of 2-(4-chlorophenyl)-7-ethoxycarbonyl-5,6,7,8-tetrahydroimidazo[2',1':2,3]thiazolo[5,4-c]pyridine, melting at 156°–159° C.

EXAMPLE 6

A mixture of 9 g of the product of Example 5 and 100 ml of a solution of hydrobromic acid in acetic acid (20% (w/w) hydrobromic acid) was heated on a boiled water bath for one hour. The precipitated crystals were filtered off and washed with n-hexane to give 9.3 g of 2-(4-chlorophenyl)-5,6,7,8-tetrahydroimidazo[2',1':2,3]thiazolo[5,4-c]pyridine dihydrobromide, melting at 304°–307° C. with decomposition.

EXAMPLE 7

A mixture of 9.1 g of 2-amino-6-ethoxycarbonyl-4,5,6,7-tetrahydrothiazolo[5,4-c]pyridine, 6.9 g of p-fluorophenacyl chloride and 100 ml of n-butanol was treated according to the procedure of Example 1 to give 6 g of 7-ethoxycarbonyl-2-(4-fluorophenyl)-5,6,7,8-tetrahydroimidazo[2',1':2,3]thiazolo[5,4-c]pyridine, melting at 164°–166° C.

The free base was treated with hydrochloric acid to give the hydrochloride, melting at 198°–203° C. with decomposition.

EXAMPLE 8

A mixture of 11 g of the hydrochloride of Example 7 and 250 ml of a solution of hydrobromic acid in acetic acid (20% (w/w) hydrobromic acid) was treated according to the procedure of Example 2 to give 11 g of 2-(4-fluorophenyl)-5,6,7,8-tetrahydroimidazo[2',1':2,3]thiazolo[5,4-c]pyridine dihydrobromide, melting at 306°–307° C. with decomposition.

The following compounds can be prepared in an analogous manner mentioned in the above Examples:

5,6,7,8-tetrahydroimidazo[2',1':2,3]thiazolo[5,4-c]pyridine, melting at 117°–118° C.; dihydrobromide, melting at 304°–305° C. with decomposition;

2-methyl-5,6,7,8-tetrahydroimidazo[2',1':2,3]thiazolo[5,4-c]pyridine;

2,3-dimethyl-5,6,7,8-tetrahydroimidazo[2',1':2,3]thiazolo[5,4-c]pyridine;

2,3-diphenyl-5,6,7,8-tetrahydroimidazo[2',1':2,3]thiazolo[5,4-c]pyridine;

2-(4-methoxyphenyl)-5,6,7,8-tetrahydroimidazo[2',1':2,3]thiazolo[5,4-c]pyridine;

2,3-bis(4-chlorophenyl)-5,6,7,8-tetrahydroimidazo[2',1':2,3]thiazolo[5,4-c]pyridine;

2-(4-methylthiophenyl)-5,6,7,8-tetrahydroimidazo[2',1':2,3]thiazolo[5,4-c]pyridine, melting at 215°–218° C.;

2-(4-methanesulfonylphenyl)-5,6,7,8-tetrahydroimidazo[2',1':2,3]thiazolo[5,4-c]pyridine, melting at 245°–248° C.;

7-ethoxycarbonyl-2-(4-nitrophenyl)-5,6,7,8-tetrahydroimidazo[2',1':2,3]thiazolo[5,4-c]pyridine, melting at 204° C.;

7-ethoxycarbonyl-5,6,7,8-tetrahydroimidazo[2',1':2,3]thiazolo[5,4-c]pyridine hydrochloride, melting at 218° C. with decomposition;

7-ethoxycarbonyl-2-methyl-5,6,7,8-tetrahydroimidazo[2',1':2,3]thiazolo[5,4-c]pyridine hydrochloride, melting at 215° C. with decomposition;

7-ethoxycarbonyl-2-(4-hydroxyphenyl)-5,6,7,8-tetrahydroimidazo[2',1':2,3]thiazolo[5,4-c]pyridine, melting at 236°–238° C.;

7-ethoxycarbonyl-2-(4-methoxyphenyl)-5,6,7,8-tetrahydroimidazo[2',1':2,3]thiazolo[5,4-c]pyridine hydrobromide, melting at 205°–206° C. with decomposition;

7-ethoxycarbonyl-2-(4-methylthiophenyl)-5,6,7,8-tetrahydroimidazo[2',1':2,3]thiazolo[5,4-c]pyridine hydrobromide, melting at 223°–224° C. with decomposition;

7-ethoxycarbonyl-2-(4-methanesulfonylphenyl)-5,6,7,8-tetrahydroimidazo[2',1':2,3]thiazolo[5,4-c]pyridine hydrobromide, melting at 230°–231° C. with decomposition;

7-(4-nitrobenzyl)-5,6,7,8-tetrahydroimidazo[2',1':2,3]-thiazolo[5,4-c]pyridine, melting at 164°-166° C.;

2-(4-hydroxyphenyl)-5,6,7,8-tetrahydroimidazo[2',1':2,3]thiazolo[5,4-c]pyridine;

2-(3,4-methylenedioxyphenyl)-5,6,7,8-tetrahydroimidazo[2',1':2,3]thiazolo[5,4-c]pyridine;

2-(4-trifluoromethylphenyl)-5,6,7,8-tetrahydroimidazo[2',1':2,3]thiazolo[5,4-c]pyridine;

2-(4-nitrophenyl)-5,6,7,8-tetrahydroimidazo[2',1':2,3]-thiazolo[5,4-c]pyridine;

2-(2-hydroxyphenyl)-5,6,7,8-tetrahydroimidazo[2',1':2,3]thiazolo[5,4-c]pyridine;

2-(4-methylphenyl)-5,6,7,8-tetrahydroimidazo[2',1':2,3]thiazolo[5,4-c]pyridine;

7-methyl-5,6,7,8-tetrahydroimidazo[2',1':2,3]-thiazolo[5,4-c]pyridine;

2,7-dimethyl-5,6,7,8-tetrahydroimidazo[2',1':2,3]-thiazolo[5,4-c]pyridine;

2,3,7-trimethyl-5,6,7,8-tetrahydroimidazo[2',1':2,3]-thiazolo[5,4-c]pyridine;

2-phenyl-7-methyl-5,6,7,8-tetrahydroimidazo[2',1':2,3]-thiazolo[5,4-c]pyridine;

2,3-diphenyl-7-methyl-5,6,7,8-tetrahydroimidazo[2',1':2,3]thiazolo[5,4-c]pyridine;

2-(4-chlorophenyl)-7-methyl-5,6,7,8-tetrahydroimidazo[2',1':2,3]thiazolo[5,4-c]pyridine;

2-(4-biphenylyl)-7-methyl-5,6,7,8-tetrahydroimidazo[2',1':2,3]thiazolo[5,4-c]pyridine;

2-(4-methoxyphenyl)-7-methyl-5,6,7,8-tetrahydroimidazo[2',1':2,3]thiazolo[5,4-c]pyridine;

2,3-bis(4-chlorophenyl)-7-methyl-5,6,7,8-tetrahydroimidazo[2',1':2,3]thiazolo[5,4-c]pyridine;

2-(4-methylthiophenyl)-7-methyl-5,6,7,8-tetrahydroimidazo[2',1':2,3]thiazolo[5,4-c]pyridine;

2-(4-methanesulfonylphenyl)-7-methyl-5,6,7,8-tetrahydroimidazo[2',1':2,3]thiazolo[5,4-c]pyridine;

2-(4-methylphenyl)-7-methyl-5,6,7,8-tetrahydroimidazo[2',1':2,3]thiazolo[5,4-c]pyridine;

2-(4-hydroxyphenyl)-7-methyl-5,6,7,8-tetrahydroimidazo[2',1':2,3]thiazolo[5,4-c]pyridine;

2-(3,4-methylenedioxyphenyl)-7-methyl-5,6,7,8-tetrahydroimidazo[2',1':2,3]thiazolo[5,4-c]pyridine;

2-(4-trifluoromethylphenyl)-7-methyl-5,6,7,8-tetrahydroimidazo[2',1':2,3]thiazolo[5,4-c]pyridine;

2-(4-nitrophenyl)-7-methyl-5,6,7,8-tetrahydroimidazo[2',1':2,3]thiazolo[5,4-c]pyridine;

7-acetyl-5,6,7,8-tetrahydroimidazo[2',1':2,3]-thiazolo[5,4-c]pyridine;

7-acetyl-2-methyl-5,6,7,8-tetrahydroimidazo[2',1':2,3]-thiazolo[5,4-c]pyridine;

7-acetyl-2,3-dimethyl-5,6,7,8-tetrahydroimidazo[2',1':2,3]thiazolo[5,4-c]pyridine;

7-acetyl-2-phenyl-5,6,7,8-tetrahydroimidazo[2',1':2,3]-thiazolo[5,4-c]pyridine;

7-acetyl-2,3-diphenyl-5,6,7,8-tetrahydroimidazo[2',1':2,3]thiazolo[5,4-c]pyridine;

7-acetyl-2-(4-chlorophenyl)-5,6,7,8-tetrahydroimidazo[2',1':2,3]thiazolo[5,4-c]pyridine;

7-acetyl-2-(4-methoxyphenyl)-5,6,7,8-tetrahydroimidazo[2',1':2,3]thiazolo[5,4-c]pyridine;

7-acetyl-2-(4-methylphenyl)-5,6,7,8-tetrahydroimidazo[2',1':2,3]thiazolo[5,4-c]pyridine;

7-acetyl-2-(4-trifluoromethylphenyl)-5,6,7,8-tetrahydroimidazo[2',1':2,3]thiazolo[5,4-c]pyridine;

7-acetyl-2-(4-nitrophenyl)-5,6,7,8-tetrahydroimidazo[2',1':2,3]thiazolo[5,4-c]pyridine;

7-acetyl-2-(3,4-methylenedioxyphenyl)-5,6,7,8-tetrahydroimidazo[2',1':2,3]thiazolo[5,4-c]pyridine;

7-acetyl-2-(4-hydroxyphenyl)-5,6,7,8-tetrahydroimidazo[2',1':2,3]thiazolo[5,4-c]pyridine;

7-acetyl-2-(4-methylthiophenyl)-5,6,7,8-tetrahydroimidazo[2',1':2,3]thiazolo[5,4-c]pyridine;

7-acetyl-2-(4-methanesulfonylphenyl)-5,6,7,8-tetrahydroimidazo[2',1':2,3]thiazolo[5,4-c]pyridine;

7-acetyl-2-(4-biphenylyl)-5,6,7,8-tetrahydroimidazo[2',1':2,3]thiazolo[5,4-c]pyridine;

7-benzoyl-5,6,7,8-tetrahydroimidazo[2',1':2,3]-thiazolo[5,4-c]pyridine;

7-benzoyl-2-methyl-5,6,7,8-tetrahydroimidazo[2',1':2,3]thiazolo[5,4-c]pyridine;

7-benzoyl-2-phenyl-5,6,7,8-tetrahydroimidazo[2',1':2,3]thiazolo[5,4-c]pyridine;

7-benzoyl-2-(4-chlorophenyl)-5,6,7,8-tetrahydroimidazo[2',1':2,3]thiazolo-[5,4-c]pyridine;

7-benzoyl-2-(4-methoxyphenyl)-5,6,7,8-tetrahydroimidazo[2',1':2,3]thiazolo-[5,4-c]pyridine;

7-benzoyl-2-(4-methylthiophenyl)-5,6,7,8-tetrahydroimidazo[2',1':2,3]thiazolo[5,4-c]pyridine;

7-benzoyl-2-(4-methanesulfonylphenyl)-5,6,7,8-tetrahydroimidazo[2',1':2,3]thiazolo[5,4-c]pyridine;

7-(4-chlorobenzoyl)-2-phenyl-5,6,7,8-tetrahydroimidazo[2',1':2,3]thiazolo[5,4-c]pyridine;

7-(4-chlorobenzoyl)-2-(4-chlorophenyl)-5,6,7,8-tetrahydroimidazo[2',1':2,3]thiazolo[5,4-c]pyridine;

7-(4-chlorobenzoyl)-2-(4-methanesulfonylphenyl)-5,6,7,8-tetrahydroimidazo[2',1':2,3]thiazolo[5,4-c]pyridine;

7-(4-nitrobenzoyl)-2-phenyl-5,6,7,8-tetrahydroimidazo[2',1':2,3]thiazolo[5,4-c]pyridine;

7-(4-nitrobenzoyl)-2-(4-chlorophenyl)-5,6,7,8-tetrahydroimidazo[2',1':2,3]thiazolo[5,4-c]pyridine;

7-phenacyl-2-phenyl-5,6,7,8-tetrahydroimidazo[2',1':2,3]thiazolo[5,4-c]pyridine;

7-(4-bromophenacyl)-2-phenyl-5,6,7,8-tetrahydroimidazo[2',1':2,3]thiazolo[5,4-c]pyridine;

7-(4-nitrophenacyl)-2-phenyl-5,6,7,8-tetrahydroimidazo[2',1':2,3]thiazolo[5,4-c]pyridine;

7-(4-methoxyphenacyl)-2-phenyl-5,6,7,8-tetrahydroimidazo[2',1':2,3]thiazolo[5,4-c]pyridine;

7-benzyl-5,6,7,8-tetrahydroimidazo[2',1':2,3]-thiazole[5,4-c]pyridine dihydrochloride hemihydrate, melting at 246°-248° C. with decomposition;

7-benzyl-2-phenyl-5,6,7,8-tetrahydroimidazo[2',1':2,3]-thiazolo[5,4-c]pyridine;

7-benzyl-2-(4-chlorophenyl)-5,6,7,8-tetrahydroimidazo[2',1':2,3]thiazolo[5,4-c]pyridine;

7-benzyl-2-(4-methoxyphenyl)-5,6,7,8-tetrahydroimidazo[2',1':2,3]thiazolo-[5,4-c]pyridine;

7-benzyl-2-(4-methylphenyl)-5,6,7,8-tetrahydroimidazo[2',1':2,3]thiazolo[5,4-c]pyridine;

7-benzyl-2-(4-methanesulfonylphenyl)-5,6,7,8-tetrahydroimidazo[2',1':2,3]thiazolo[5,4-c]pyridine;

7-(2-chlorobenzyl)-5,6,7,8-tetrahydroimidazo[2',1':2,3]-thiazolo[5,4-c]pyridine dihydrochloride dihydrate, melting at 227°-228° C. with decomposition;

7-(2-chlorobenzyl)-2-phenyl-5,6,7,8-tetrahydroimidazo[2',1':2,3]thiazolo[5,4-c]pyridine, melting at 135° C.;

7-(4-nitrobenzyl)-2-phenyl-5,6,7,8-tetrahydroimidazo[2',1':2,3]thiazolo[5,4-c]pyridine;

7-(4-nitrobenzyl)-2-(4-chlorophenyl)-5,6,7,8-tetrahydroimidazo[2',1':2,3]thiazolo[5,4-c]pyridine;

7-(4-nitrobenzyl)-2-(4-biphenylyl)-5,6,7,8-tetrahydroimidazo[2',1':2,3]thiazolo[5,4-c]pyridine;

7-(4-nitrobenzyl)-2-(4-methylthiophenyl)-5,6,7,8-tetrahydroimidazo[2',1':2,3]thiazolo[5,4-c]pyridine;

7-formyl-2-phenyl-5,6,7,8-tetrahydroimidazo[2',1':2,3]-thiazolo[5,4-c]pyridine;

7-(4-nitrobenzyl)-2-(4-methanesulfonylphenyl)-5,6,7,8-tetrahydroimidazo[2',1':2,3]thiazolo[5,4-c]pyridine;

7-nitroso-2-phenyl-5,6,7,8-tetrahydroimidazo[2',1':2,3]-thiazolo[5,4-c]pyridine;

benzyl [2-phenyl-5,6,7,8-tetrahydroimidazo[2',1':2,3]-thiazolo[5,4-c]pyridin-7-yl]phenylacetate; and 7-(α-carboxybenzyl)-2-phenyl-5,6,7,8-tetrahydroimidazo[2',1':2,3]thiazolo[5,4-c]pyridine.

EXAMPLE 9

A mixture of 5.1 g of 2-phenyl-5,6,7,8-tetrahydroimidazo[2',1':2,3]thiazolo[5,4-c]pyridine, 10 g of 10% palladium carbon and 150 ml of mesitylene was refluxed with heating for 19 hours. After the catalyst was filtered off, the solvent was distilled off. To the residue was added n-hexane and crystals were filtered off. The crude crystals were recrystallized from ethyl acetate to give 2.7 g of 2-phenylimidazo[2',1':2,3]-thiazolo[5,4-c]pyridine, melting at 183°–185° C.

The following compounds can be prepared in an analogous manner mentioned in the above Example 9:

imidazo[2',1':2,3]thiazolo[5,4-c]pyridine, melting at 120°–121° C.;

2-methylimidazo[2',1':2,3]thiazolo[5,4-c]pyridine;

2,3-dimethylimidazo[2',1':2,3]thiazolo[5,4-c]pyridine;

2,3-diphenylimidazo[2',1':2,3]thiazolo[5,4-c]pyridine;

2-(4-chlorophenyl)imidazo[2',1':2,3]thiazolo[5,4-c]pyridine;

2-(2,4-dichlorophenyl)imidazo[2',1':2,3]thiazolo[5,4-c]pyridine;

2-(4-biphenylyl)imidazo[2',1':2,3]thiazolo[5,4-c]pyridine;

2-(4-methoxyphenyl)imidazo[2',1':2,3]thiazolo[5,4-c]pyridine;

2,3-bis(4-chlorophenyl)imidazo[2',1':2,3]thiazolo[5,4-c]pyridine;

2-(4-methylthiophenyl)imidazo[2',1':2,3]thiazolo[5,4-c]pyridine;

2-(4-methanesulfonylphenyl)imidazo[2',1':2,3]-thiazolo[5,4-c]pyridine;

2-(4-methylphenyl)imidazo[2',1':2,3]thiazolo[5,4-c]pyridine;

2-(4-hydroxyphenyl)imidazo[2',1':2,3]thiazolo[5,4-c]pyridine;

2-(3,4-methylenedioxyphenyl)imidazo[2',1':2,3]-thiazolo[5,4-c]pyridine;

2-(4-trifluoromethylphenyl)imidazo[2',1':2,3]-thiazolo[5,4-c]pyridine;

2-(4-nitrophenyl)imidazo[2',1':2,3]thiazolo[5,4-c]pyridine; and 2-(2-hydroxyphenyl)imidazo[2',1':2,3]thiazolo[5,4-c]pyridine.

Although the present invention has been adequately discussed in the foregoing specification and examples included therein, one readily recognizes that various changes and modifications may be made without departing from the spirit and scope thereof.

What is claimed is:

1. A heterocyclic compound of the formula:

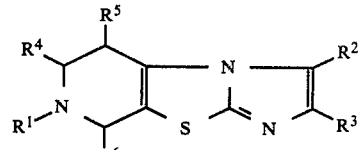

or a pharmaceutically acceptable acid addition salt thereof, wherein $R^1$ is hydrogen, $C_{1-4}$ alkyl, $C_{1-4}$ alkoxycarbonyl, formyl, nitroso, $C_1-C_4$ alkanoyl, benzoyl, phenylacetyl, phenacyl, phenyl $C_1-C_4$ alkyl, α-(benzyloxycarbonyl)benzyl or α-carboxybenzyl; each of $R^2$ and $R^3$ is hydrogen, $C_{1-4}$ alkyl or phenyl; all of $R^4$, $R^5$ and $R^6$ are hydrogens, or both $R^1$ and $R^6$, and $R^4$ and $R^5$ together form single bonds; in which definitions the term "benzoyl", "phenylacetyl", "phenacyl", "phenyl $C_1-C_4$ alkyl" or "phenyl" means that it may be substituted by at least one substituent at any position(s) on the aromatic nucleus, each substituent being independently selected from $C_{1-4}$ alkyl, $C_{1-4}$ alkoxy, halogen, hydroxyl, phenyl, nitro, trifluoromethyl, methylthio, methanesulfonyl and methylenedioxy.

2. The compound of claim 1 wherein $R^2$ is hydrogen and $R^3$ is hydrogen or phenyl which may be substituted by at least one substituent at any position(s) on the aromatic nucleus, each substituent being independently selected from $C_{1-4}$ alkyl, $C_{1-4}$ alkoxy, halogen, hydroxyl, phenyl, nitro, trifluoromethyl, methylthio, methanesulfonyl and methylenedioxy.

3. The compound of claim 1 wherein $R^2$ is hydrogen and $R^3$ is hydrogen or phenyl which is unsubstituted or substituted by halogen, nitro or methylthio.

4. The compound of claim 1:
7-ethoxycarbonyl-2-(4-nitrophenyl)-5,6,7,8-tetrahydroimidazo[2',1':2,3]thiazolo[5,4-c]pyridine.

5. The compound of claim 1:
7-ethoxycarbonyl-2-phenyl-5,6,7,8-tetrahydroimidazo[2',1':2,3]thiazolo[5,4-c]pyridine.

6. The compound of claim 1:
7-ethoxycarbonyl-2-(4-fluorophenyl)-5,6,7,8-tetrahydroimidazo[2',1':2,3]thiazolo[5,4-c]pyridine.

7. The compound of claim 1:
7-ethoxycarbonyl-2-(4-methylthiophenyl)-5,6,7,8-tetrahydroimidazo[2',1':2,3]thiazolo[5,4-c]pyridine.

8. The compound of claim 1:
2-(4-fluorophenyl)-5,6,7,8-tetrahydroimidazo[2',1':2,3]thiazolo[5,4-c]pyridine.

9. The compound of claim 1:
2-(4-methylthiophenyl)-5,6,7,8-tetrahydroimidazo[2',1':2,3]thiazolo[5,4-c]pyridine.

10. The compound of claim 1:
7-(2-chlorobenzyl)-2-phenyl-5,6,7,8-tetrahydroimidazo[2',1':2,3]thiazolo[5,4-c]pyridine.

11. The compound of claim 1:
7-(4-nitrobenzyl)-5,6,7,8-tetrahydroimidazo[2',1':2,3]thiazolo[5,4-c]pyridine.

12. The compound of claim 1:
2-phenylimidazo[2',1':2,3]thiazolo[5,4-c]pyridine.

13. A pharmaceutical composition for treating immune diseases comprising an effective amount of the compound of claim 1 in combination with a pharmaceutically acceptable inert carrier or adjuvant.

* * * * *